United States Patent [19]

DeOrio et al.

[11] Patent Number: 5,681,316
[45] Date of Patent: Oct. 28, 1997

[54] TIBIAL RESECTION GUIDE

[75] Inventors: James K. DeOrio, Jacksonville, Fla.; Lisanne Aimee Eng, Quincy, Mass.

[73] Assignee: Johnson & Johnson Professional, Inc., Raynham, Mass.

[21] Appl. No.: 697,334

[22] Filed: Aug. 22, 1996

[51] Int. Cl.$^6$ .................................................. A61B 17/56
[52] U.S. Cl. .................................. 606/88; 606/87
[58] Field of Search .......................... 606/79, 80, 86–89, 606/96, 102

[56] References Cited

U.S. PATENT DOCUMENTS

| | | | |
|---|---|---|---|
| 4,736,737 | 4/1988 | Fargie et al. | 128/92 |
| 4,952,213 | 8/1990 | Bowman et al. | 606/79 |
| 5,275,603 | 1/1994 | Ferrante et al. | 606/86 |
| 5,342,368 | 8/1994 | Petersen | 606/88 |
| 5,431,656 | 7/1995 | Clift, Jr. et al. | 606/86 |
| 5,520,692 | 5/1996 | Ferrante | 606/80 |

OTHER PUBLICATIONS

Brochure entitled Specialist® Intramedullary Tibial Alignment System, *Surgical Technique*, Johnson & Johnson Orthopaedics, Specialist® I.M. Tibia Instruments Designed in consultation with Johnson & Johnson Orthopaedics, Inc. and William Petty, M.D., Peter F. Gearen, M.D., and Gary J. Miller, Ph.D., pp. 1–11, 1988.

Brochure Johnson & Johnson Orthopaedics, *Surgical Technique*, Revision Surgery for Failed Total–Knee Replacement, P.F.C.® Modular Total Knee Systems with Specialist® Revision Instruments, pp. 10–11, 1994®.

Brochure entitled Surgical Technique for Use with P.F.C.® Knee Systems, Johnson & Johnson Orthopaedics, *Primary Cruciate–Retaining Procedure*, Specialist® 2 Instruments, pp. 53–55, The I.M. Tibial Alignment Guide, 1996.

*Primary Examiner*—Michael Buiz
*Assistant Examiner*—David O. Reip
*Attorney, Agent, or Firm*—Nutter, McClennen & Fish, LLP

[57] ABSTRACT

A tibial resection guide is adapted to be mated with a tibial cutting guide block. The tibial resection guide enables the cutting guide block and its cutting surface to be manipulated vertically and horizontally. Further, the device enables the cutting guide block to be angularly oriented in the anteroposterior plane and in the mediolateral plane. The tibial resection guide of the invention is adapted for use with an intramedullary alignment rod.

22 Claims, 6 Drawing Sheets

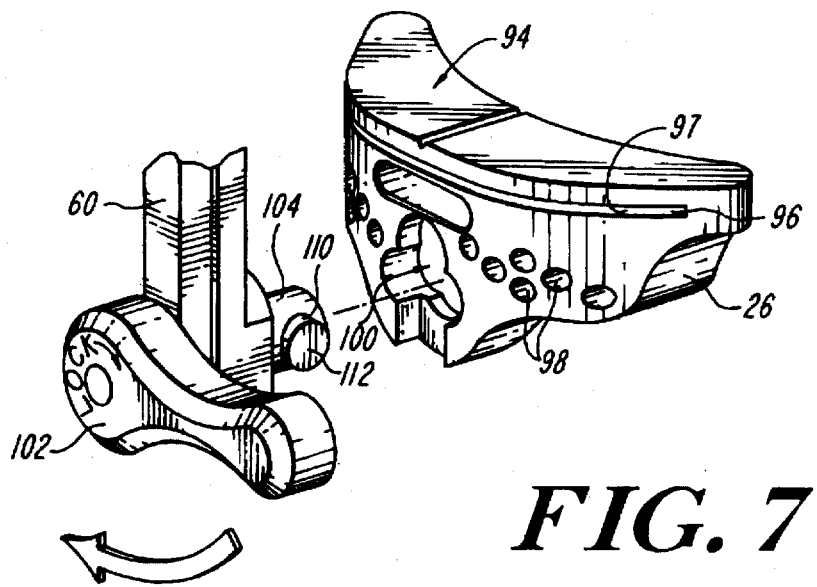
FIG. 7
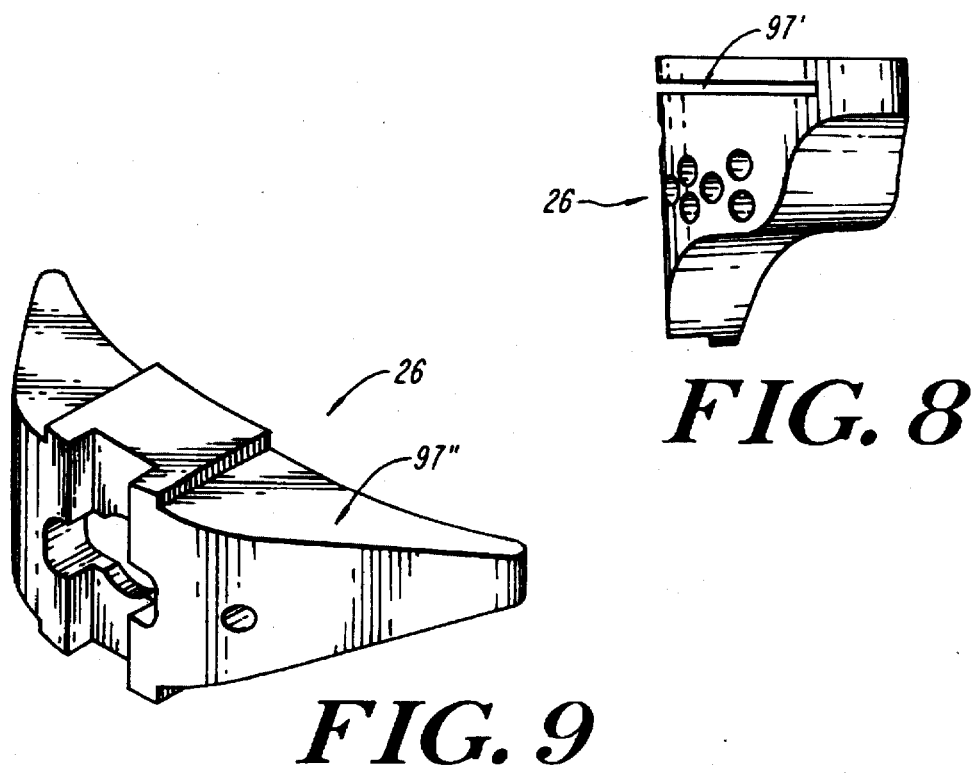
FIG. 8
FIG. 9

TIBIAL RESECTION GUIDE

BACKGROUND OF THE INVENTION

The invention relates to a cutting guide to facilitate accurate resection of the proximal tibia during total knee arthroplasty.

Total knee arthroplasty typically involves replacing the articulating surfaces of the distal femur, the proximal tibia, and the posterior side of the patella with prosthetic components. Preparation of the joint surfaces determines the placement of the implant components and is critical to the success of the surgery.

The proximal tibia, or the tibial plateau, must be properly prepared to accept the prosthetic components that mount upon the tibia during total knee arthroplasty. The proximal tibial must be resected to provide a bony surface having the proper shape to accept the tibial components of a knee prosthesis. The resection must often be made with a specific anteroposterior slope and/or a specific mediolateral slope. Variable patient anatomies preclude the use of a standard resection cut in the anteroposterior direction and/or the mediolateral direction. Similarly, the amount of bone that is to be removed from the tibia varies among patients. For these reasons, it is essential that tibial cutting guides have sufficient versatility to help a surgeon to easily and accurately determine the cut that best suits a given patient, and to guide the surgeon while effecting resection of the tibia.

Various types of cutting guides are known to serve as jigs to enable a surgeon to accurately resect the proximal tibia during arthroplasty procedures. Exemplary devices are described in U.S. Pat. Nos. 4,736,737; 5,275,603; 5,342,368; and 5,431,656. Product bulletins published by various manufacturers also describe known tibial resection guides. (See, Johnson & Johnson Orthopaedics, "Surgical Technique: P.F.C.® Modular Total Knee System with SPECIALIS® Revision Instruments (1994); and Johnson & Johnson Orthopaedics, SPECIALIS® Intramedullary Tibial Alignment System.") Such cutting guides help to improve the accuracy and reliability of tibial resection procedures. However, more versatile devices are needed to facilitate tibial resection procedures that are appropriate to a patient's anatomy. It would be most desirable to provide a single resection guide which, while easy to use, is able to accommodate virtually any necessary tibial resection.

Accordingly, it is an object of the invention to provide a tibial resection guide that has sufficient versatility to accommodate the anatomical differences among a variety of patients. The further object is provide such a resection guide that can be used to determine and effect with accuracy virtually any necessary proximal resection of the tibia. It is also an object to provide such a resection guide that provides improved accuracy and ease of use. Further objects will be apparent to those having ordinary skill in the art upon reading the following disclosure.

SUMMARY OF THE INVENTION

The tibial resection guide of the invention provides enhanced versatility and ease of use. The resection guide enables a removable and replaceable cutting guide block, which is attached to the resection guide device, to be oriented vertically with respect to the remaining components of the guide device, and horizontally (in the anteroposterior plane) with respect to an intramedullary alignment rod. Moreover, the resection guide device enables the cutting guide block to be angularly oriented to effect a tibial resection with an anteroposterior slope at an angle ranging from about 0° to 10°, sloping down from anterior to posterior. The same resection guide device also enables the cutting guide block to be oriented to achieve a tibial resection that is oriented in the mediolateral plane at an angle of about 0° to 4°. Such mediolateral orientation may be adjusted to attain a slope from the medial to lateral side, or from the lateral to medial side.

The guide further includes a vertical mounting assembly including a first, pivotal member and a second, non-pivotal member. The first and second members are joined to one another such that the first member is able to rotate with respect to the second member in the mediolateral plane. The vertical mounting assembly is slidably engaged by a slot formed in a horizontal mounting assembly to enable vertical movement of the vertical mounting assembly with respect to the horizontal mounting assembly. Such vertical movement effects a corresponding vertical adjustment of the attached cutting guide block. Preferably, a vertical adjustment mechanism interfaces between the vertical and horizontal mounting assemblies to selectively control the vertical position of the cutting guide block.

The resection guide further includes a vertically oriented sleeve having a bore that is coaxial with a longitudinal axis thereof. The aperture is adapted to be placed upon an alignment rod, such as an intramedullary alignment rod, to facilitate mounting of the guide on the alignment rod. A horizontal mounting rod is appended to and extends traverse to the longitudinal axis of the sleeve element. The mounting rod is adapted to be inserted through an aperture formed in a mounting block of the guide. In this manner the mounting block, can be attached as a unit to the alignment rod. Further, the mounting block is hingedly connected to a portion of the horizontal mounting assembly, providing rotation in the anterior-posterior plane.

BRIEF DESCRIPTION OF THE DRAWINGS

FIG. 7 schematically illustrates a locking mechanism useful with the tibial cutting guide of the invention.

FIG. 8 is a side view of a cutting guide block having an anteroposterior sloping cutting surface.

FIG. 9 is a perspective view of a cutting guide block having a mediolateral sloping cutting surface.

DETAILED DESCRIPTION OF THE INVENTION

Figure 1:
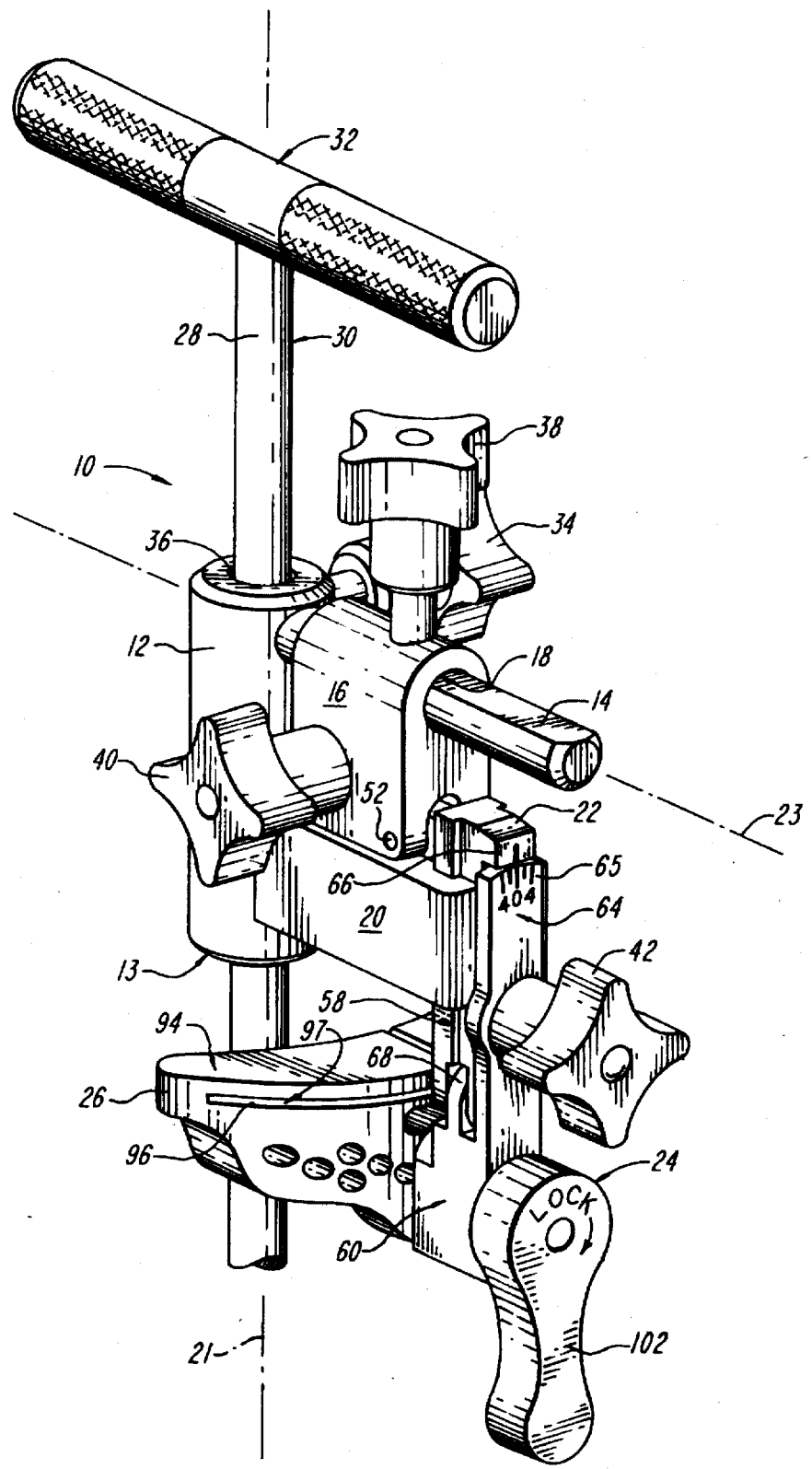
FIG. 1 is a perspective view of a tibial resection guide constructed according to the present invention and mounted upon an intramedullary rod.

The tibial resection guide 10 of the present invention is useful in that it represents a single cutting tool that may be adjusted vertically, horizontally, at an anteroposterior angle, and at a mediolateral angle. Guide 10 has a longitudinal axis 21, and includes a vertically oriented mounting sleeve 12 having attached thereto a horizontal mounting rod 14. A mounting block 16 has a horizontally extending aperture 18 formed therein for receiving the horizontal mounting rod 14, and enabling the mounting block 16 to mount thereon. A horizontal mounting assembly 20 pivotally mounts upon a lower portion of mounting block 16. A vertical mounting assembly 22 is in turn, slidably engaged with horizontal mounting member 20 at a top portion thereof. A bottom portion of the vertical mounting assembly 22 includes a locking element 24 for mounting and engaging a tibial cutting guide block 26.

As shown in FIG. 1, the sleeve 12 of the cutting guide 10 can be mounted upon an alignment rod such as an intramedullary rod 28. Intramedullary rod 28 includes a shaft 30 and a proximal handle 32, which may be removably mounted upon the shaft 28. A thumbscrew element 34, or a similar securing means, may be used to restrict the inner diameter of a bore 36 formed in the sleeve 12 to secure the guide 10 at a desired vertical position on intramedullary rod 28. Gross, preliminary vertical adjustment of the guide with respect to the intramedullary rod 28 and a patient's tibia may be made by manipulating thumbscrew 34 to select a desired vertical position of the guide on the intramedullary rod 28.

In a preferred embodiment the bottom edge 13 of sleeve 12 is aligned with the cutting surface 97 of cutting guide block 26 during initial vertical positioning. Subsequent adjustments, as described below, can be made to alter the vertical position of cutting surface 97 with respect to bottom edge 13.

Similarly, the guide 10 may be adjusted horizontally with respect to the intramedullary rod 28 by controlling the position of mounting block 16 on the horizontal mounting rod 14. Thumbscrew 38, or a similar securing means, may restrict the inner diameter of aperture 18 to selectively position and secure the mounting block 16 on horizontal mounting rod 14.

Thumbscrew 40, or a similar securing means, can be used to selectively control the anteroposterior slope of the cutting surface of the tibial cutting guide block 26. Similarly, thumbscrew 42, or a similar securing element, can be used to selectively control the mediolateral angulation of the cutting surface of the tibial cutting guide block 26.

Figure 2:
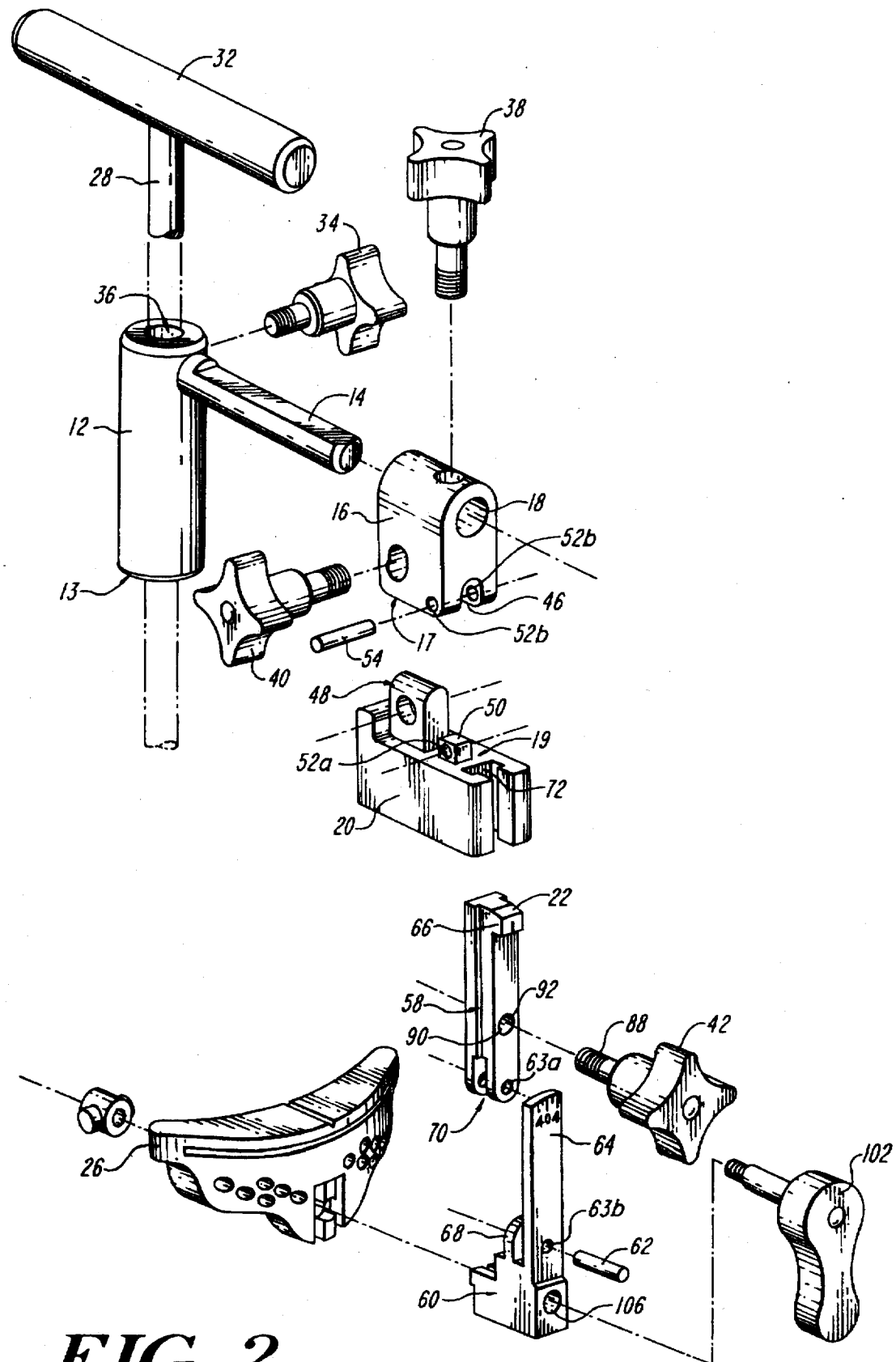
FIG. 2 is an exploded view of the tibial resection guide shown in FIG. 1.
Figure 4:
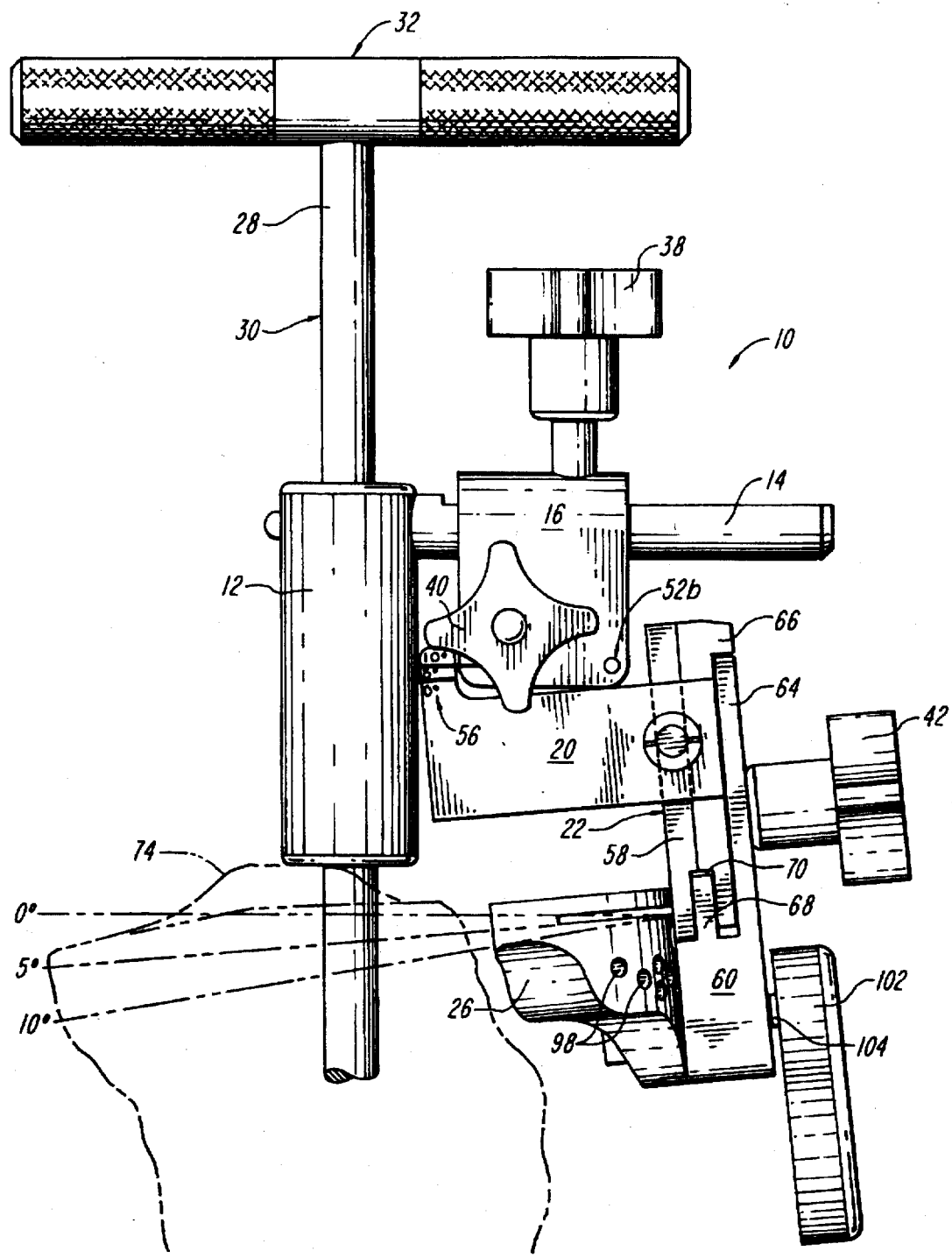
FIG. 4 is a side view of the tibial resection guide of FIG. 1.

FIGS. 2 and 4 illustrate a preferred embodiment in which mounting block 16 includes a ventral surface 17 having a first slot (not shown) and a second, smaller slot 46. Horizontal mounting assembly 20 has a dorsal surface 19 that includes protrusions 48 and 50 that are intended to fit within slots 44 and 46, respectively. Protrusion 48 is generally larger than protrusion 50 and is adapted to fit within the first, larger slot formed in ventral surface 17. Protrusion 50, which is smaller than protrusion 48, includes a transverse aperture 52a. Protrusion 50 is adapted to fit within slot 46. A dowel 54 is inserted through aperture 52a and aperture 52b formed in protrusion 50 to provide a pivot point for the horizontal mounting assembly with respect to the mounting block 16. Manipulation of thumbscrew 40 controls the degree of interference and locking power exerted upon protrusion 48. Loosening of thumbscrew 40 enables protrusion 48 to be at least partially extended from slot 44, thereby enabling the horizontal mounting assembly to rotate with respect to the horizontal mounting block 16 about dowel 54 which serves as a pivot point. This rotation action allows the cutting guide block 26 to be moved between a normal position of 0° anteroposterior slope to a maximum sloped condition (e.g., about 10° of slope from anterior to posterior sides). A gauge element 56 can be formed on the mounting block 16 and horizontal mounting assembly 20 to indicate the degree of anteroposterior slope at which the cutting surface of the cutting guide block 26 is oriented.

As noted above, the resection guide 10 may be oriented such that the slope of the top surface 94 and cutting surface 97 of cutting guide block 26 are oriented at an angle between about 0° and 10°, sloping downwardly from the anterior to the posterior edges of surface 94. A resection cut having an anteroposterior angle greater than ten degrees may be achieved, if necessary, by using a cutting guide block which has a pre-angled cutting surface, as described below and illustrated in FIGS. 8 and 9.

Figure 3:
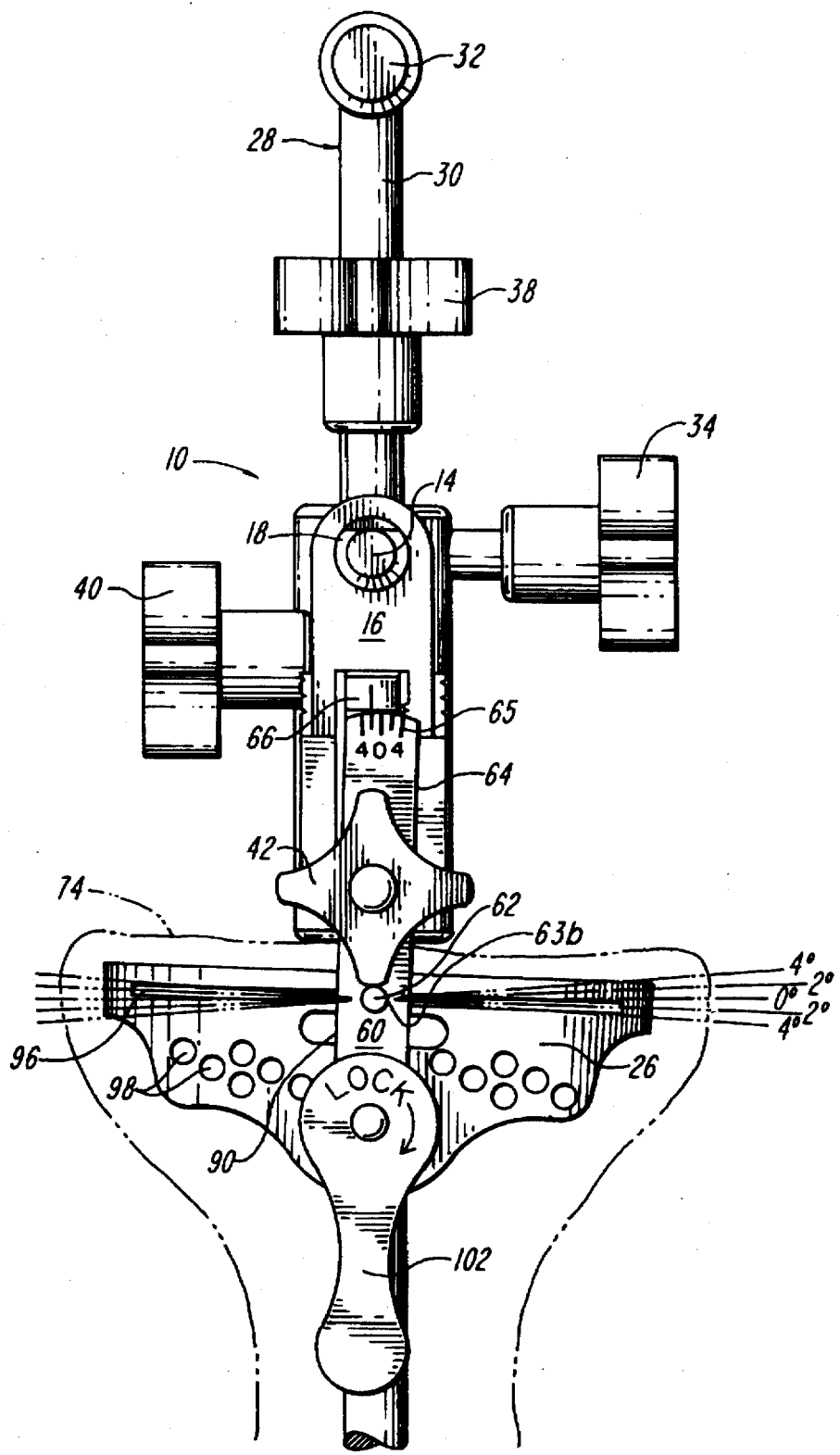
FIG. 3 is a front view of the tibial resection guide shown in FIG. 1.

As illustrated in FIGS. 1–3, the vertical mounting assembly 22, includes separate upper 58 and lower 60 segments which are pivotally joined to each other by a dowel 62, which extends through apertures 63a, 63b formed in segments 58 and 60. The pivotal connection between segments 58 and 60 is such that the lower segment is able to pivot side-to-side, in the mediolateral direction.

In one embodiment segments 58 and 60 are interlocked with each other. FIGS. 1, 2, and 4 illustrate that lower segment 60 includes a front elongate member 64 which extends to an upper portion of upper segment 58, terminating adjacent overhang 66 of segment 58. A protrusion 68 is disposed on segment 60, rearward of front elongate member 64. The protrusion 68 is adapted to fit within a slot 70 formed in a bottom end of segment 58. The protrusion 68 is fitted within slot 70 such that apertures 63a, 63b are aligned, enabling dowel 62 to be inserted therein.

The upper segment 58 of the vertical mounting assembly 22 is mounted upon the horizontal mounting block 20 by insertion of the upper segment 58 within vertically oriented slot 72 formed in horizontal mounting assembly 20. Preferably, the upper segment 58 is slidably engaged with slot 72, enabling vertical adjustment of the vertical mounting member 22 (and the cutting guide block 26) independent of movement of the remaining components of guide 10.

Figure 5:
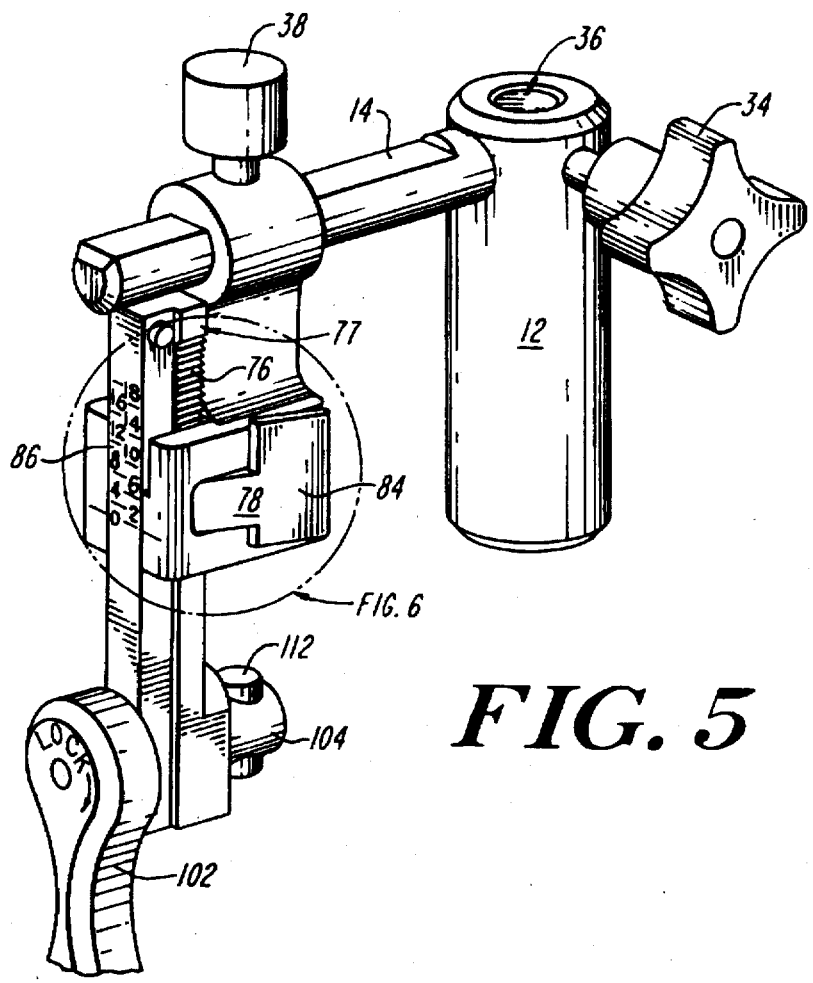
FIG. 5 is a perspective view of a portion of the tibial resection guide of the invention, illustrating a vertical adjustment mechanism.
Figure 6:
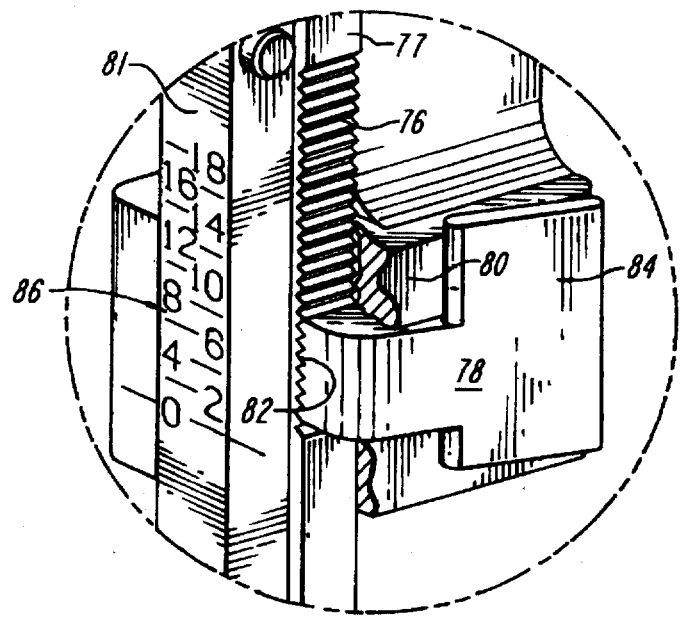
FIG. 6 is a detailed view of the vertical adjustment mechanism of FIG. 5.

Fine vertical adjustment of the vertical mounting assembly 22, and hence the cutting guide block 26, is important to accurately and easily position the cutting surface 97 of the cutting guide block 26 for proper resection of the proximal tibia 74. Various engagement mechanisms can be utilized to selectively control the vertical movement and positioning of vertical mounting assembly 22 with respect to horizontal mounting assembly 20. In one embodiment, illustrated in FIGS. 5 and 6, a pawl and detent mechanism is utilized to control such fine vertical movements. A plurality of detent elements 76 is formed on a side surface 77 of upper segment 58 of vertical mounting assembly 22. A pawl element 78 is formed on an adjacent sidewall 80 of horizontal mounting assembly 20. Preferably, the pawl has one or more teeth 82 which are adapted to engage and interlock with the detents 76 on sidewall 77. In a preferred embodiment, the pawl 78 is biased to a position in which the pawl teeth 82 positively engage and interlock with detents 76. It is not possible to move the vertical mounting assembly 22 independent of horizontal mounting assembly 20 when the teeth 82 of pawl 78 are positively engaged with detents 76. Independent movement of vertical mounting assembly 22 may be effected by depressing pawl tab 84, thereby removing the engagement between teeth 82 and detents 76. The vertical mounting assembly 22 may then be adjusted to the desired position. Indicia 86 may be present on side wall 77 or front wall 81 to indicate the vertical position of the device.

Ordinarily, it is sufficient to design the tibial resection guide device to provide free vertical adjustment to range between 0 and 20 mm, preferably in one or two millimeter increments. One of ordinary skill in the art will readily appreciate, however, that minor modifications can be made to the device to permit greater or less free vertical adjustment.

The resection guide device 10 of the invention also facilitates rapid orientation of the cutting surface 97 of the cutting guide block 26 at a desired angle in the mediolateral plane. The device may be adjusted to resect the proximal tibia at a mediolateral angle with a slope directed from the medial to the lateral side, or from the lateral to the medial side. The range of mediolateral slope typically is from about 0° to 4°. However, greater angulation can be achieved, if desired, by using cutting guide blocks which have a cutting surface that is pre-angled in either the medial to lateral or lateral to medial directions.

FIG. 8 illustrates a cutting guide block 26 having a cutting surface 97' that has an predetermined anteroposterior slope. FIG. 9 illustrates a cutting guide block 26 having a cutting surface 97" that has a predetermined mediolateral slope.

As noted above, the vertical mounting member 22 is formed of upper and lower segments 58, 60, which are pivotally joined to each other. Preferably, the upper segment 58 is maintained normal to the transverse axis 23 of guide 10. Dowel 62 enables the lower segment 60 and the attached cutting guide block 26 to be pivoted with respect to the upper segment 58. Pivoting of the lower segment 60 alters the angle in the mediolateral plane at which cutting guide block 26 is oriented.

The angle at which the cutting guide block 26 is oriented in the mediolateral plane can be selectively adjusted and controlled by a variety of mechanisms. One preferred mechanism, illustrated in FIGS. 1-3, utilizes a threaded member 88, which is embedded in the upper segment 58 and which extends transversely from upper segment 58 through an aperture 90. Aperture 90 can be a horizontally elongated aperture or an oversized circular aperture formed in the front elongated member 64 of lower segment 60. A thumbscrew 42, or similar device, can be threaded upon threaded member 88. Thumbscrew 42 can be tightened to constrain movement of the front elongated member 64 with respect to upper segment 58. Conversely, the thumbscrew 42 can be loosened to allow pivotal movement of the lower segment 60 with respect to upper segment 58. The pivotal movement of the upper segment 60 is limited by the abutment of front elongate member 64 against sidewalls 92 of aperture 90. Preferably, the aperture 90 is elongated or oversized to the extent necessary to permit up to about 4° of angulation and the mediolateral plane. One of ordinary skill in the art will readily appreciate that minor modifications may be made to the structure to permit further angulation.

The cutting guide blocks useful with the tibial resection guide device of the invention are standard tibial cutting blocks, commercially available from Johnson & Johnson Professional, Inc. of Raynham, Mass., Preferably SPECIALIST® 2 cutting blocks are useful with guide device 10. As illustrated in FIG. 7, guide block 26 includes a top surface 94 having a horizontally elongate transverse slot 96 disposed therebelow, which is adapted to receive a saw blade that is used to resect the tibia. Surface 97 represents the cutting surface of the guide block. A plurality of transversely oriented bores 98 extend through the body of guide block 26, below slot 96, to assist in securing the guideblock to the tibia when the remainder of the guide 10 is removed from a patient. Such guide blocks are available with a cutting surface 97 that is substantially horizontal, angled from anterior to posterior, angled from medial to lateral, or angled from lateral to medial. The guide block 26 also includes a locking aperture 100 that is disposed at a bottom portion thereof. The aperture 100 is preferably horizontally elongated.

A variety of locking elements 24 can be used to secure guide block 26 to lower segment 60. In one embodiment, illustrated in FIG. 7, the locking element is a key-like structure that allows quick connection and disconnection of the guideblock 26. The key-like locking structure includes a lock handle 102, which is rotatable between a locked, vertical position and an unlocked, horizontal position, offset by 90° from the locked position. A horizontal dowel 104, extends from a front end which is attached to handle 102 through a lower aperture 106 formed in the lower segment 60. A back end 108 of dowel 104 includes an aperture 110 within which is disposed a smaller locking dowel 112, which is oriented perpendicular to dowel 104. In the unlocked position the locking dowel 112 is able to slide through locking aperture 100 in the cutting guide block 26 to enable block 26 to be mated to the guide 10. Once mated, lock handle 102 is rotated 90° to lock the guide block 26 by re-orienting the locking dowel 112 to be vertically positioned, thereby preventing its removal through locking aperture 100. One or more compression gaskets or washers (not shown) may be used to facilitate proper locking of the locking element.

One skilled in the art will readily appreciate the operation of and the advantages of the tibial cutting guide device of the invention. The device preferably is used with an intramedullary alignment rod. Initially, a bore is drilled into the intramedullary canal of a patient's tibia. The guide then is then mounted upon the intramedullary rod 28 by inserting the rod through mounting sleeve 12. Thumbscrew 34 is tightened to secure the entire instrument at a desired vertical location upon the intramedullary rod, thus establishing the initial position of the guide. Additionally, fine vertical adjustment of the guide 10 may be made subsequently by depressing the pawl tab 84 to remove the engagement between detent 76 and teeth 82 of pawl 78. Once this engagement is removed, the vertical mounting element 22 may be moved vertically, independent of the remaining components of the guide 10.

Horizontal adjustment of guide 10 in the anteroposterior plane can be effected by loosening thumbscrew 38, thereby enabling the mounting block 16 to slide horizontally upon horizontal mounting rod 14. Such movement allows the tibial cutting guide 10 to be positioned against the anterior aspect of the tibia. Once the desired horizontal position is achieved, thumbscrew 38 can be tightened to secure the device in position.

Rotation, or angulation, of the cutting surface 97 of the cutting guide block 26 in the anteroposterior plane can be effected by loosening thumbscrew 40, thereby allowing horizontal mounting assembly 20 (together with the attached vertical mounting assembly 22 and cutting guide block 26) to be rotated with respect to the mounting member 16. The horizontal mounting assembly 20 rotates about dowel 54, which serves as a pivot point. Such rotation determines the slope of the cutting surface 97 of the tibial cutting guide from anterior to posterior. Preferably, angular increments are indicated by markings 56 placed on a sidewall of mounting member 16. Upon obtaining the desired posterior slope, thumbscrew 40 is tightened to maintain the guide in this desired position. Any anteroposterior angle greater than that which is typically afforded by the cutting guide device alone can be achieved by utilizing a cutting block which has a cutting surface which is pre-angled in the anteroposterior direction.

Mediolateral rotation of the cutting surface 97 of the cutting guide block 26 can be achieved by loosening thumbscrew 42 to permit movement of lower segment 60, front elongate member, 64, and cutting guide block 26 with respect to upper segment 58. This movement results from pivoting of the lower segment 60 with respect to the upper segment 58 about dowel 62, which serves as a pivot point. Such rotation corresponds to the varus-valgus orientation of the tibial resection. Preferably, the guide device 10 includes markings 65 on the front elongate member 64 and overhangs 66 to indicate angular orientations in the mediolateral plane between about 0° and 4°.

Upon achieving the overall desired orientation of the tibial cutting guide, Steinmann pins (not shown) are inserted into bores 98 of the cutting block 26 and into the tibia, thereby fixing the cutting guide block 26 against the anterior surface of the tibia in the desired orientation. The remaining components of the guide 10, together with intramedullary rod 28, are removed, leaving only the cutting guide block 26 in place. At this point the tibial resection can be accomplished by simply inserting a reciprocating saw, or a similar device, through transverse slot 96 to resect the tibia.

One of ordinary skill will appreciate that various modifications may be made to the invention described and claimed herein without exceeding the scope of the invention. Moreover, the entirety of all cited references is expressly incorporated by reference herein.

What is claimed is:

1. A tibial resection guide device, comprising:
   a vertical mounting assembly including a first, pivotal member and a second, non-pivotal member, the first, pivotal member being able to rotate, with respect to the second member, in the mediolateral plane;
   a horizontal mounting assembly having a vertically oriented slot disposed therein to receive at least a portion of the vertical mounting assembly to facilitate vertical displacement of the vertical mounting assembly and an attached cutting guide block with respect to the horizontal mounting assembly;
   a vertical adjustment mechanism disposed on the vertical mounting assembly to selectively control the vertical position of the vertical mounting assembly and the cutting guide block with respect to the horizontal mounting assembly;
   a locking mechanism for removably securing the tibial cutting guide block to the vertical mounting assembly;
   a vertically oriented sleeve element having a longitudinal axis extending therethrough, the sleeve element being adapted to mount the resection guide device to an alignment rod;
   a mounting rod appended to and extending from the sleeve element transverse to the longitudinal axis of the sleeve element;
   a mounting block having on one surface thereof a horizontally oriented aperture disposed therein that is adapted to receive the mounting rod and to mount the mounting block upon the mounting rod in a slidable condition, and a means disposed on another surface thereof for securing the mounting block to the horizontal mounting assembly; and
   a pivot hinge which pivotally joins at least a portion of the horizontal mounting assembly to the mounting block such that the horizontal mounting assembly, the vertical mounting assembly, and the tibial cutting guide block are all able to rotate as a unit in the anteroposterior plane with respect to the mounting block.

2. The device of claim 1, further comprising:
   a tibial cutting guide block having a transverse slot extending therethrough to define a cutting surface, a plurality of apertures extending transversely therethrough, and a mounting aperture extending therethrough, the tibial cutting guide block being removably and replaceably matable with the tibial resection guide device by way of the locking mechanism.

3. The device of claim 1 wherein the cutting surface of the tibial cutting block is substantially horizontal.

4. The device of claim 1 wherein the cutting surface of the tibial cutting block is angled such that it slopes downwardly from an anterior edge thereof to a posterior edge thereof.

5. The device of claim 1 wherein the cutting surface of the tibial cutting block is angled in the mediolateral direction such that it slopes downwardly from a medial edge of the block to a lateral edge of the block.

6. The device of claim 1 wherein the cutting surface of the tibial cutting block is angled in the mediolateral direction such that it slopes downwardly from a lateral edge of the block to a medial edge of the block.

7. The device of claim 1 wherein the vertical mounting assembly further comprises a first protrusion that extends from the first member, the first protrusion being pivotally secured by a dowel within a slot formed in the second member to facilitate rotation in the mediolateral plane of the first member with respect to the second member.

8. The device of claim 7 wherein the vertical mounting assembly further comprises a second, longer protrusion which extends from the first member along a front surface of the second member.

9. The device of claim 8 wherein the cutting guide block mounts upon the first member of the vertical mounting assembly.

10. The device of claim 9 wherein the locking mechanism is a screw connection.

11. The device of claim 9 wherein the locking mechanism comprises
   a horizontally elongated aperture formed in the cutting block;
   a first dowel, having first and second ends, extending through the first member;
   a handle mechanism, secured to the first end of the dowel and adapted to rotate the dowel 90° between locked and unlocked positions; and
   a second dowel, extending transverse to the first dowel, disposed in the second end of the first dowel.

12. The device of claim 8 further comprising a mediolateral rotation control element actuatable between a first condition to enable mediolateral rotation of the first member with respect to the second member, and a second condition to prevent mediolateral rotation.

13. The device of claim 12 wherein the mediolateral rotation control element is a thumbscrew mechanism which comprises (i) a threaded rod extending from within the second member through and beyond a horizontally elongated aperture formed in the second protrusion of the first member, and (ii) a knob which is mounted upon an end of the threaded rod that extends from the aperture of the second protrusion.

14. The device of claim 12 further comprising a gauge element associated with the second element, the gauge element cooperating with an indicator element formed upon the second protrusion to indicate the degree of mediolateral rotation.

15. The device of claim 8 wherein the horizontal mounting assembly further comprises:

a first, large protrusion, on a top surface thereof, which is slidably disposed within a first slot formed in the mounting block;

a second, lower protrusion which mounts within a second, smaller slot formed in the mounting block; and a dowel extending through the second protrusion and an adjacent portion of the mounting block to enable rotation of the horizontal mounting assembly in the anterior-posterior plane with respect to the mounting block.

16. The device of claim 15 wherein a rotation control element extends between the mounting block and the horizontal mounting assembly to control rotation of the horizontal mounting assembly with respect to the mounting block.

17. The device of claim 16 wherein the rotation control element is a thumbscrew.

18. The device of claim 1 wherein the sleeve element includes a securement mechanism to selectively secure the device in a desired vertical position on the alignment rod.

19. The device of claim 18 wherein the securement mechanism is a thumbscrew.

20. The device of claim 18 wherein the alignment rod is an intramedullary alignment rod.

21. The device of claim 1 wherein the vertical adjustment mechanism comprises a plurality of detents formed on a side portion of the second vertical member and a pawl mechanism having one or more teeth and being biased to engage the detents, the pawl mechanism being mounted on a side portion of the horizontal mounting assembly.

22. A tibial resection guide device, comprising:

a horizontal mounting assembly having a means for slidably receiving at least a portion of a vertical mounting assembly to facilitate vertical displacement of the vertical mounting assembly and an attached cutting guide block independent of any vertical movement of the horizontal mounting assembly;

a vertical mounting assembly including at least one portion thereof that is rotatable, independent of the remaining components of the guide, in the mediolateral plane;

a vertical adjustment mechanism disposed on the vertical mounting assembly to selectively control the vertical position of the vertical mounting assembly and the cutting guide block with respect to the horizontal mounting assembly;

a locking means for removably securing the tibial cutting guide block to the vertical mounting assembly;

a clamp element adapted to mount the resection guide device to an alignment rod;

a mounting element appended to the clamp element;

a mounting block, slidably connected to the mounting element to facilitate horizontal movement of the mounting block toward and away from the alignment rod; and a pivotal connection element connecting at least a portion of the horizontal mounting assembly to the mounting block such that the horizontal mounting assembly and the vertical mounting assembly are all able to rotate as a unit in the anteroposterior plane with respect to the mounting block.

* * * * *